(12) United States Patent
Nakatani et al.

(10) Patent No.: US 8,557,195 B2
(45) Date of Patent: Oct. 15, 2013

(54) SENSOR SUBSTRATE AND ARRAY SUBSTRATE USING THE SAME

(75) Inventors: Masaya Nakatani, Hyogo (JP); Makoto Takahashi, Osaka (JP); Takuya Oka, Kyoto (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 13/620,365

(22) Filed: Sep. 14, 2012

(65) Prior Publication Data

US 2013/0017979 A1 Jan. 17, 2013

Related U.S. Application Data

(63) Continuation of application No. PCT/JP2011/002566, filed on May 9, 2011.

(30) Foreign Application Priority Data

May 11, 2010 (JP) ................................. 2010-108876

(51) Int. Cl.
*G01N 21/75* (2006.01)

(52) U.S. Cl.
USPC ........... 422/400; 422/119; 422/416; 422/503; 422/553; 422/430; 422/401; 422/420; 422/421; 422/422; 422/423; 422/424; 422/425; 422/426; 422/427; 422/428; 422/429; 422/68.1; 422/82.05; 422/82.06; 436/164; 436/169; 436/170; 435/13; 435/283.1; 435/287.1; 435/287.8; 435/287.9; 435/288.7; 435/287.7

(58) Field of Classification Search
USPC ......... 422/119, 416, 503, 553, 430, 400, 401, 422/420, 421, 422, 423, 424, 425, 426, 427, 422/428, 429, 68.1, 82.05, 82.06; 436/164, 436/169, 170; 435/13, 283.1, 287.1, 287.7, 435/287.8, 287.9, 288.7; 1/119, 416, 503, 1/553, 430, 400, 401, 420, 421, 422, 423, 1/424, 425, 426, 427, 428, 429, 68.1, 1/82.05, 82.06
See application file for complete search history.

(56) References Cited

U.S. PATENT DOCUMENTS

2003/0119034 A1 6/2003 Kang et al.
2005/0038498 A1 2/2005 Dubrow et al.
(Continued)

FOREIGN PATENT DOCUMENTS

EP 1620256 A2 2/2006
EP 2 172 415 A1 4/2010
(Continued)

OTHER PUBLICATIONS

Written Opinion of the International Searching Authority issued in International Patent Application No. PCT/JP2011/002566 dated May 11, 2010.

*Primary Examiner* — Dennis M White
(74) *Attorney, Agent, or Firm* — McDermott Will & Emery LLP (57) ABSTRACT

A sensor substrate includes a base and fibrous projections on an upper surface of the base. The fibrous projections have fixed ends fixed to the upper surface of the base and free ends opposite to the fixed ends, respectively. The fibrous projections provide a fixed end-side region including the fixed ends and a free end-side region including the free ends. The total surface area at which the fibrous projections in the fixed end-side region is larger than that in the free end-side region.

18 Claims, 5 Drawing Sheets

(56) References Cited

U.S. PATENT DOCUMENTS

| | | |
|---|---|---|
| 2005/0221072 A1 | 10/2005 | Dubrow et al. |
| 2008/0014630 A1 | 1/2008 | Furuki |
| 2010/0004695 A1 | 1/2010 | Stad et al. |
| 2010/0219488 A1 | 9/2010 | Nakatani et al. |
| 2011/0111984 A1 | 5/2011 | Nakatani et al. |
| 2011/0232794 A1 | 9/2011 | Nakatani et al. |

FOREIGN PATENT DOCUMENTS

| | | |
|---|---|---|
| EP | 1725189 A4 | 3/2011 |
| JP | 2003-315349 A | 11/2003 |
| JP | 2003-322653 A | 11/2003 |
| JP | 2006-045668 A | 2/2006 |
| JP | 2007-526439 A | 9/2007 |
| JP | 2007-533371 A | 11/2007 |
| JP | 2008-020412 A | 1/2008 |
| JP | 2010-183900 A | 8/2010 |
| JP | 2010-208885 A | 9/2010 |
| WO | WO-2004/099068 A3 | 4/2005 |
| WO | WO-2005/084582 A1 | 9/2005 |
| WO | WO-2008/103464 A1 | 8/2008 |
| WO | WO-2007/078304 A3 | 12/2008 |
| WO | WO-2009/034697 A1 | 3/2009 |
| WO | WO-2010/004695 A1 | 1/2010 |
| WO | WO-2010/082279 A1 | 7/2010 |

SENSOR SUBSTRATE AND ARRAY SUBSTRATE USING THE SAME

This application is a continuation of International Application PCT/JP2011/002566, filed May 9, 2011, claiming the foreign priority of Japanese Patent Application No. 2010-108876, filed May 11, 2010, the contents of which are incorporated herein by reference.

TECHNICAL FIELD

The present disclosure relates to a sensor substrate used for a filter for, e.g. DNA analysis or protein analysis and an array substrate, such as a DNA array substrate or a protein array substrate, including the sensor substrate.

BACKGROUND ART

In recent years, as an example of a sensor substrate, in the medical and pharmaceutical fields (e.g., drug development, clinical diagnosis), array substrates have been used for various analyses such as gene analysis, Single Nucleotide Polymorphism (SNPs) analysis, or an analysis of the interaction between substances.

An array substrate is mainly used for a bio-array substrate. The array substrate includes plural sensor substrates having regions including reaction fields in which an interaction occurs. The sensor substrates are arranged in an array. Target substances are fixed to respective reaction fields and then sample solution is dripped thereon. As a result, the interaction between the detection substance and the target substance contained in the sample is promoted. Then, the interaction level can be detected based on the fluorescence intensity and can be used for an analysis.

In order to improve the sensitivity at which the substance is detected, the sensor substrate is required to increase the interaction strength in the reaction field in which the interaction with the detection substance occurs. On the other hand, in order to form a reaction field on the sensor substrate, a method has been widely used in which a probe substance selectively coupled to the detection substance is absorbed in the surface of the sensor substrate. In order to increase the interaction strength in the reaction field, it is required to increase the amount of the probe substance absorbed in the surface of the sensor substrate (i.e., to increase the amount of the probe per unit area). However, there is a limit on the amount of the probe that can be absorbed per unit area. In another method, the interaction strength is increased by increasing the surface area of the sensor substrate. For example, the surface of the sensor substrate functioning as a reaction field is caused to be rough and porous. Alternatively, the surface area can be increased by adhering porous material, such as agarose, nitrocellulose or glass fiber, to the sensor substrate. By these methods, the sensor substrate can have an increased surface area to increase the absorbed amount of the probe substance, thus increasing the interaction strength in the reaction field.

In conventional sensor substrate, however, a spot diameter within which liquid permeates may be undesirably expanded or droplets may be repelled. Accordingly, an accurate analysis may be difficult, thus resulting in declined detection accuracy.

SUMMARY

A sensor substrate includes a base and fibrous projections on an upper surface of the base. The fibrous projections have fixed ends fixed to the upper surface of the base and free ends opposite to the fixed ends, respectively. The fibrous projections provide a fixed end-side region including the fixed ends and a free end-side region including the free ends. The total surface area at which the fibrous projections in the fixed end-side region is larger than that in the free end-side region. This sensor substrate has high detection accuracy.

DETAIL DESCRIPTION OF PREFERRED EMBODIMENTS

Exemplary Embodiment 1

Figure 1:
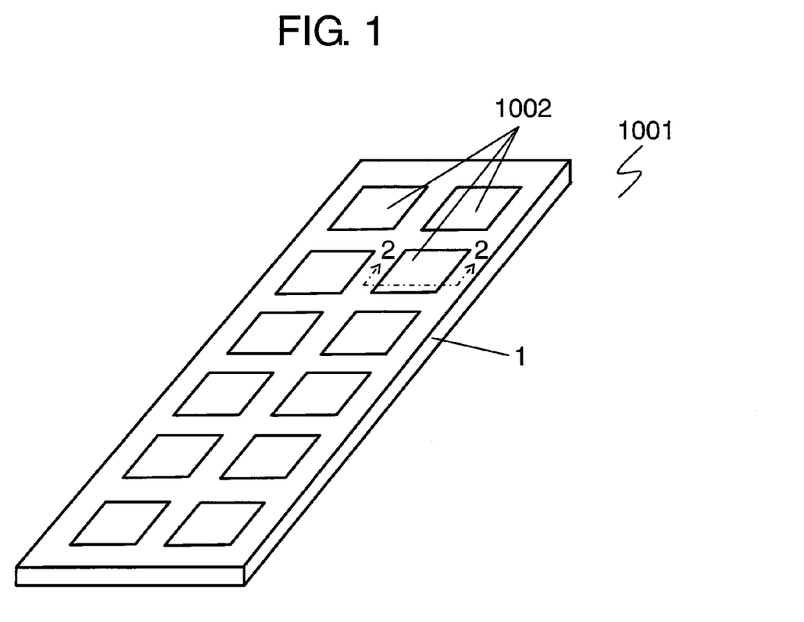
FIG. 1 is a top perspective view of an array substrate including a sensor substrate according to Exemplary Embodiment 1 of the present disclosure.

FIG. 1 is a top perspective view of array substrate 1001 according to Exemplary Embodiment 1 of the present disclosure. Array substrate 1001 includes substrate 1 made of silicon and sensor substrates 1002 arranged on substrate 1 in an array. Each of sensor substrates 1002 has a reaction field.

Figure 2:
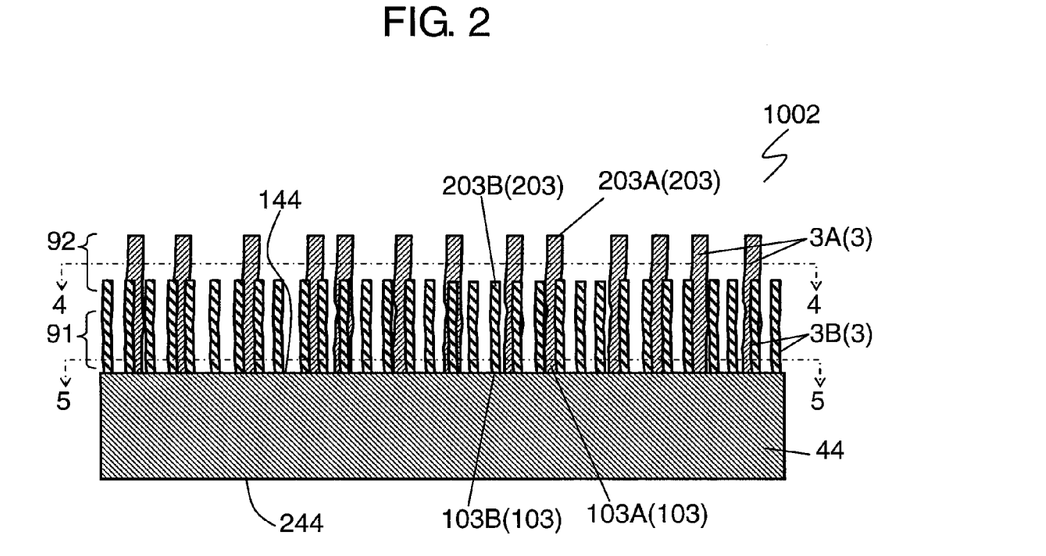
FIG. 2 is a cross-sectional view of the sensor substrate along line 2-2 shown in FIG. 1.

FIG. 2 is a cross-sectional view of array substrate 1001 (sensor substrates 1002) along line 2-2 shown in FIG. 1. Sensor substrate 1002 has a side length or a diameter ranging about from 100 µm to 300 µm. Sensor substrate 1002 includes base 44 made of, for example, silicon, and fibrous projections 3 directly joined to upper surface 144 of base 44. Fibrous projection 3 mainly contains silicon oxide. The term, "directly joined" means a condition in which fibrous projections 3 are directly formed on base 44 and atoms or molecules constituting base 44 and fibrous projections 3 are directly coupled to each other. In this condition, the molecules are generally covalently-linked to one another. According to Embodiment 1, silicon atoms at the surface (upper surface) 144 of base 44 are covalently-linked to silicon atoms in fibrous projection 3 via oxygen atoms in the atmosphere.

A surface at which base 44 is joined to fibrous projection 3 has thereon no adhesive agent and does not include any material other than atoms or molecules constituting base 44 and fibrous projections 3.

Base 44 is a silicon substrate made of single crystal silicon, but may be made of polycrystalline silicon, amorphous silicon, or glass.

Fibrous projection 3 is made mainly of silicon oxide material, such as silicon oxide and preferably made of amorphous silicon dioxide. Fibrous projection 3 has a diameter ranging about from 0.01 µm to 1 µm.

Fibrous projections 3 have fixed ends 103 fixed to surface 144 of base 44 and free ends 203 opposite to fixed ends 103. Fibrous projections 3 provide fixed end-side region 91 in which fixed ends 103 are positioned and free end-side region 92 in which free ends 203 are positioned. Free end-side region 92 is located farther away from surface 144 of base 44 than fixed end-side region 91 is. No free end 203 is positioned in fixed end-side region 91. No fixed end 103 is positioned in free end-side region 92.

Fibrous projections 3 include fibrous projections 3B and fibrous projections 3A longer than fibrous projections 3B.

Figure 3A:
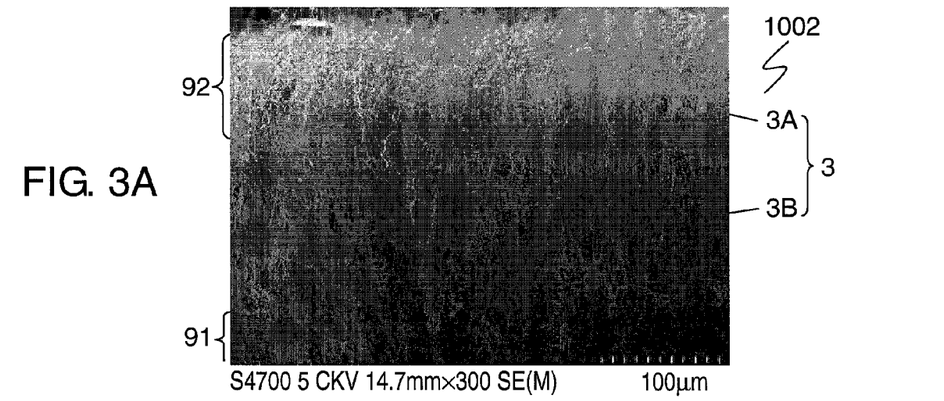
FIG. 3A is an enlarged view of the sensor substrate according to Embodiment 1.
Figure 3B:
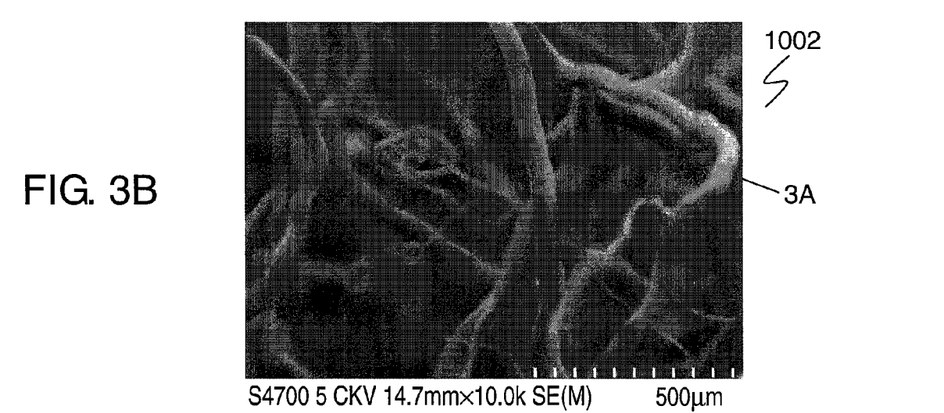
FIG. 3B is an enlarged view of the free end-side region of the sensor substrate shown in FIG. 3A.
Figure 3C:
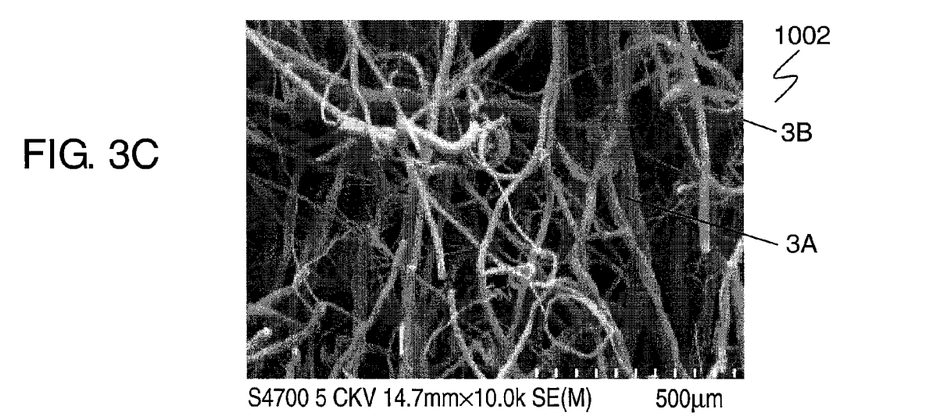
FIG. 3C is an enlarged view of the fixed end-side region of the sensor substrate shown in FIG. 3A.

FIGS. 3A to 3C are enlarged view of sensor substrate 1002, and are photographs taken by a scanning electron microscope (SEM). FIG. 3B is a SEM photograph of free end-side region 92 of sensor substrate 1002 shown in FIG. 3A. FIG. 3C is a SEM photograph of fixed end-side region 91 of sensor substrate 1002 shown in FIG. 3A.

Figure 4:
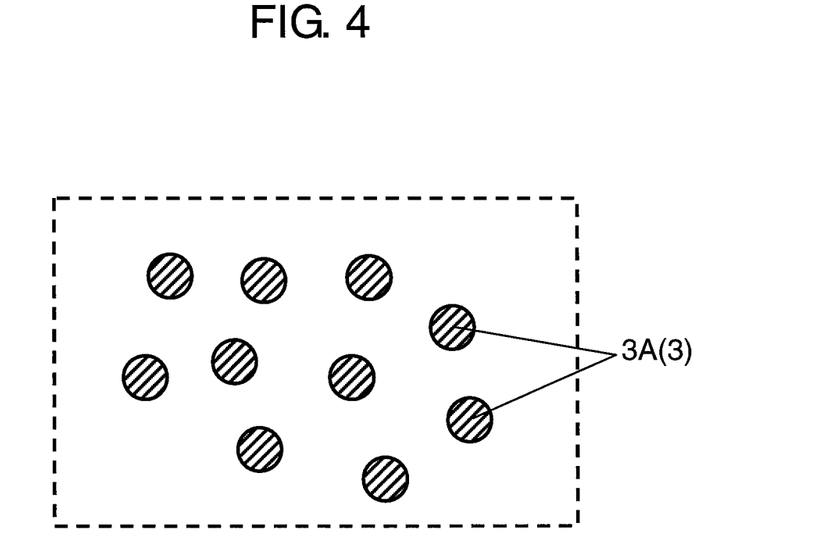
FIG. 4 is a cross-sectional view of the sensor substrate along line 4-4 shown in FIG. 2.
Figure 5:
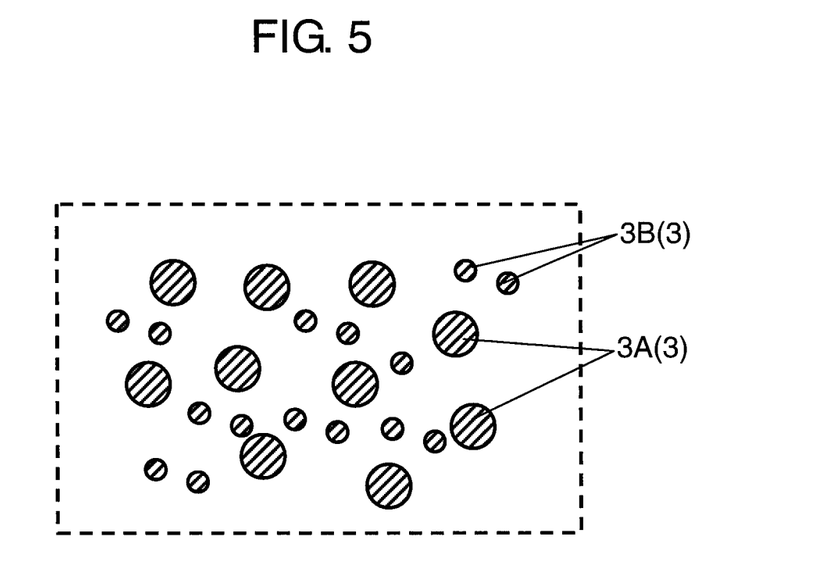
FIG. 5 is a cross-sectional view of the sensor substrate shown along line 5-5 shown in FIG. 2.

FIG. 4 is a cross-sectional view of sensor substrate 1002 along line 4-4 shown in FIG. 2 and is a cross-sectional view of fibrous projections 3 in free end-side region 92. FIG. 5 is a cross-sectional view of sensor substrate 1002 along line 5-5 shown in FIG. 2 and is a cross-sectional view of fibrous projections 3 in fixed end-side region 91. Free end-side regions 92 mainly have long fibrous projections 3A therein. Fixed end-side region 91 has long fibrous projections 3A and short fibrous projections 3B mixed with long fibrous projections 3A.

A density which is the number of fibrous projections 3 per unit area in fixed end-side region 91 (the sum of the numbers of fibrous projections 3A and 3B) is higher than a density which is the number of fibrous projections 3A per unit area in free end-side region 92. In sensor substrate 1002 according to Embodiment 1, free end-side region 92 desirably has fibrous projections 3A at a density lower than $10000/mm^2$ and fixed end-side region 91 desirably has fibrous projection 3 at a density higher than $10000/mm^2$. Thus, the total surface area which is the sum of the surface areas of fibrous projections 3 existing in fixed end-side region 91 (total surface area of fibrous projections 3A and 3B) is larger than the total surface area of fibrous projections 3 existing in free end-side region 92. Thus, when liquid is applied, the total surface area of fibrous projections 3 contacting the liquid is larger in fixed end-side region 91 than in free end-side region 92.

Fibrous projections 3 are arranged at intervals that are narrower in fixed end-side region 91 than in free end-side region 92. In sensor substrate 1002 according to Embodiment 1, free end-side region 92 desirably has fibrous projections 3A arranged at intervals not smaller than 1 μm. On the other hand, fixed end-side region 91 desirably has fibrous projections 3 arranged with at intervals smaller than 1 μm.

This configuration allows the liquid to diffuse at a lower diffusion rate in fixed end-side region 91 than in free end-side region 92.

In a certain region including fibrous projections 3, a porosity is defined as a ratio of the volume of a part around fibrous projections 3 that is not occupied by fibrous projections 3 to the volume of the certain region. Free end-side region 92 desirably has a porosity higher than that of fixed end-side region 91. In sensor substrate 1002 according to Embodiment 1, free end-side region 92 has a porosity not smaller than 90% and fixed end-side region 91 has a porosity smaller than 90%.

Fibrous projection 3A desirably has a diameter larger than that of fibrous projection 3B. In sensor substrate 1002 according to Embodiment 1, fibrous projection 3A has a diameter not smaller than 150 nm and fibrous projection 3B has a diameter smaller than 150 nm. A larger diameter decreases the density which is the number of fibrous projections 3 per unit area, thus resulting in a smaller total surface area. A smaller diameter increases the density of fibrous projections, thus resulting in a larger total surface area.

Free end-side region 92 having a high diffusion rate desirably has a width that is equal to or shorter than a half of the height from surface 144 of base 44 to free end 203A of fibrous projection 3A.

Fibrous projections 3 may be closely-spaced so as to be entangled with one another or also may be branched in various directions. Fibrous projections 3 entangled with one another and branched into plural twigs makes fibrous projections 3 strong. Alternatively, fibrous projections 3 may extend in the same direction.

From the viewpoint of productivity, substrate 1 and base 44 are desirably made of the same material. Alternatively, substrate 1 may be made of resin and has a recess therein to have sensor substrate 1002 therein.

A method of manufacturing sensor substrate 1002 according to Embodiment 1 will be described below. The configuration of the present disclosure is not limited by the manufacture method described hereinafter. First, fibrous projections 3 are formed on base 44.

A catalyst material, for example, Pt is sputtered to surface 144 of base 44 to form a catalyst layer. The catalyst layer made of Pt desirably has a thickness ranging from about 1 nm to 20 nm. This thickness is adjusted to control the diameter or the growth rate of fibrous projections 3. Then, base 44 is heat-treated in an atmosphere of the temperature ranging from 1000° C. to 1200° C. and an oxygen partial pressure ranging from 1 Pa to 1000 Pa, thereby micronizing the catalyst layer to form fibrous projections 3 on base 44. Considering the productivity or the heat resistance of fibrous projection 3, the above thermal treatment is more preferably carried out in the atmosphere of the temperature ranging from 1100° C. to 1200° C. and the oxygen partial pressure ranging from 10 Pa to 200 Pa.

In this thermal treatment, the temperature rising rate during a temperature rising process can be adjusted to obtain particulate catalysts having different sizes on base 44. For example, when the temperature rising rate is about 1000° C./min, large particles and small particles can be both obtained, thus resulting in a difference in the density in the length direction or a difference in the diameter of fibrous projections 3. By adjusting the thickness of the catalyst layer or the temperature rising rate as described above, fibrous projections 3 that have different length distributions and densities can be obtained. Fibrous projection 3 is made from silicon at surface 144 of base 44 and oxygen supplied during the thermal treatment. Thus, surface 144 of base 44 is directly joined strongly to fibrous projections 3.

Different densities and diameters of fibrous projections 3 can be obtained not only adjusting the thickness or the size of the catalyst layer but also the other parameters.

For example, by controlling the oxygen partial pressure, the structure of fibrous projections 3 can be changed. Fibrous projections 3 can be formed along the direction in which the oxygen gas is diffused in the thermal treatment. A high oxygen partial pressure causes crimpy fibrous projections 3 to be closely-spaced and entangled. A low oxygen partial pressure arranges causes fibrous projections 3 to extend in the same direction.

As such, by appropriately changing the oxygen concentration to form fibrous projections 3, fibrous projections 3 can be obtained that have different length distributions and densities. For example, fibrous projections 3A firstly grow with a low oxygen concentration and then a high oxygen concentration can be used to grow short fibrous projections 3B. Alternatively, a high oxygen concentration may be used to cause short fibrous projections 3B to grow and then a low oxygen concentration can be used to cause long fibrous projections 3A to grow.

The area where the fibrous projections 3 are formed can also be controlled. The forming of fibrous projection 3 can be suppressed by forming a layer made of silicon dioxide at a part of surface 144 of base 44 made of silicon. Thus, even when the layer made of silicon dioxide has a catalyst layer thereon, fibrous projections 3 are not formed from the catalyst layer. By forming a catalyst layer only at a desired position, fibrous projections 3 can be formed only at a desired position.

The catalyst layer is made of Pt, but may be made of Fe, Co, Ni, or Au to provide a desired shape.

According to Embodiment 1, a method of forming fibrous projections 3 by depositing the catalyst layer on base 44, other methods also may be used. For example, fibrous projections 3 can be formed from a seed layer formed on surface 144 of base 44.

An effect of sensor substrate 1002 according to Embodiment 1 will be described.

The conventional sensor substrate may have detection accuracy decline as described below.

As porous material used for increasing the surface area, a hydrophilic structure is used. The hydrophilic porous material causes liquid including probe substance to be dripped on a reaction field at a high diffusion rate. Thus, the liquid permeates to an unnecessary range, thus resulting in a wide-range absorption of the probe substance. The region including a reaction field expands to an unnecessary range. As a result, the region has a reduced absorption amount of the probe substance per unit area, and consequently interaction strength of the reaction field decreases, thus also decreasing detection sensitivity.

On the other hand, a structure having low hydrophilicity may be used in a region including a reaction field. In this case, however, dripped liquid is repelled by the surface of the structure. Thus, the absorption amount of the probe substance does not reach a required amount, which causes an ununiform reaction field, thus failing to provide an accurate determination of the concentration.

When the sensor substrates are arranged in an array shape to provide an array substrate and when the sensor substrates have high hydrophilicity in the reaction fields of the surface, liquid expanded to an unnecessary range may cause the liquid to be mixed with the reaction field of the surface of neighboring sensor substrate located at a neighboring position. Accordingly, different reaction fields cannot have a small distance between the fields when different types of probe substances are formed in the respective reaction fields. As a result, many different reaction fields cannot be formed on a single array substrate.

When the spot diameter within which liquid permeates is undesirably expanded or when droplets are undesirably repelled, an accurate analysis is prevented, thus causing the sensor substrate to have detection accuracy decline.

In contrast to the conventional sensor substrate, sensor substrate 1002 according to Embodiment 1 includes fibrous projections 3 having a diameter ranging from 0.01 μm to 1 μm. Thus, a sufficiently-large surface area can be secured, thus improving the sensitivity.

Furthermore, by allowing free end-side region 92 and fixed end-side region 91 to have fibrous projections 3 at significantly-different densities, a liquid diffusion rate becomes higher in free end-side region 92 than in fixed end-side region 91. As a result, liquid is not repelled and is captured by fibrous projections 3A in free end-side region 92. Liquid of sample solution is suppressed from diffusing by fibrous projections 3B in fixed end-side region 91.

As a result, when the detection substance fixed by fibrous projections 3 of sensor substrates 1002 of array substrate 1001 interacts with sample solution, the solution is prevented from having an expanded spot diameter and is securely trapped on fibrous projections 3, thus securely providing the interaction between the detection substance and the sample. The interaction level can be securely detected based on, e.g., a fluorescence intensity. This provides an accurate analysis. As such, sensor substrates 1002 and array substrate 1001 have a high detection accuracy.

Furthermore, fibrous projections 3 mainly contain silicon oxide. Thus, fibrous projections 3 have low fluorescence intensity, thus suppressing noise generation. Furthermore, since silicon oxide is stable material, silicon oxide can be subjected to various surface treatments. Furthermore, as described above, fibrous projections 3 can be formed by a single process and thus are superior in productivity.

Figure 6:
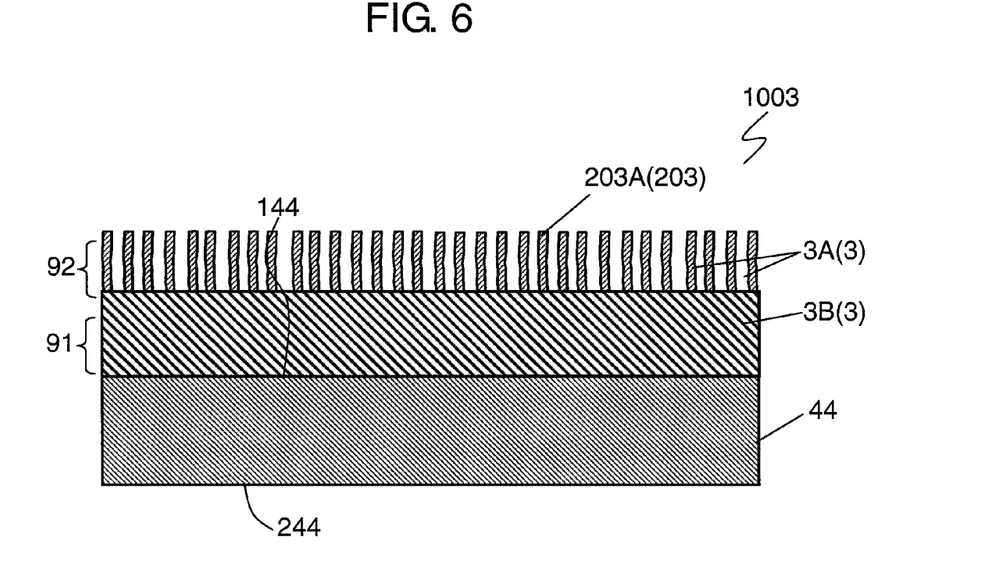
FIG. 6 is a cross-sectional view of another sensor substrate according to Embodiment 1.

FIG. 6 is a cross-sectional view of another example of sensor substrate 1003 according to Embodiment 1. In FIG. 6, components identical to those of sensor substrate 1002 shown in FIG. 2 are denoted by the same reference numerals.

In sensor substrate 1003 shown in FIG. 6, fibrous projections 3B of sensor substrate 1002 shown in FIG. 2 are densely formed or partially fused to one another to form fixed end-side region 91 having a mesh-like structure. Thus, fixed end-side region 91 has a lower porosity than free end-side region 92, while free end-side region 92 has a high porosity. By allowing Si gas generated from base 44 to react with oxygen diffused from the gas phase so as to form fibrous projections 3 on surface 144 of side base 44, it is possible to provide different densities in the cross-sectional direction of fibrous projections 3. This configuration allows fibrous projections 3 to have a large total surface area per a unit area.

In the above configuration, a thermal treatment is firstly performed to form fibrous projections 3 (3A, 3B) at a temperature ranging from 1000° C. to 1100° C. Then, the temperature is raised to a temperature not lower than 1200° C. to cause fibrous projections 3 (3A, 3B) in fixed end-side region 91 to be thermally fused, thus providing fibrous projections 3 (3A, 3B) having the mesh arrangement.

Alternatively, different densities of the projections in the length direction can be provided by changing the growing conditions of fibrous projections 3 by appropriately changing the oxygen concentration during the formation of fibrous projections 3, for example.

When silicon particles instead of Pt are attached to surface 144 of base 44 and are subjected to a thermal treatment, fibrous projections 3 can also be formed. This method allows base 44 made of material, such as glass, other than silicon to have fibrous projections 3 thereon. Thus, fibrous projections 3 can be formed without catalyst.

The silicon particles may be made of silicon, silicon monoxide, or silicide of alloy of silicon. Silicon particles preferably have a small diameter not larger than 5 μm. The small silicon particles can increase the evaporation amount of silicon required to form fibrous projections 3. By subjecting base 44 having silicon particles attached thereto to a thermal treatment under a high temperature and a low oxygen concentration as described above, fibrous projections 3 can be formed without catalyst.

The silicon monoxide particles can provide fibrous projections 3 even when the temperature is about 900° C., which is lower than the above temperature. A low oxygen concentration may desirably be, for example, an oxygen partial pressure not higher than about 50 Pa at a total pressure ranging from 1000 Pa to 5000 Pa.

In the above thermal treatment of base 44, it is preferable to perform the temperature rising process under the atmosphere including a minimum amount of oxygen, and after the temperature rising process, to perform a temperature-maintaining process under atmosphere with a low oxygen partial pressure with a small amount of oxygen. With there thermal processes, it is possible to suppress formation of an oxide film on the silicon substrate, and therefore to improve productivity of fibrous projections 3.

In the above method, fibrous projections 3 are made from silicon particles and oxygen supplied during the thermal treatment. This can consequently eliminate the need for a crystalline silicon wafer, thus allowing sensor substrate 1002 to be inexpensive.

Furthermore, fibrous projections 3 can be formed on bases 44 made of various materials depending on an application. When fibrous projections 3 is formed on base 44 made of transparent material, such as sapphire or glass (quartz), light transmitting therein can be observed and the positioning is also simplified for example, thus providing improved operability.

Alternatively, fibrous projections 3 can be formed on base 44 made of a flexible material, such as a glass fiber sheet.

Alternatively, fibrous projections 3 also can be easily formed only at desired positions by mixing silicon particles with, e.g. binder to place silicon particles only at desired positions by, e.g. printing or an ink jet method.

When fibrous projections 3 are made of silicon particles, fibrous projections 3 can be formed without using base 44 made of silicon. For example, when silicon particles are subjected to atmosphere of a low oxygen concentration and a high temperature as described in Embodiment 1, the silicon particles evaporate to cause a chemical reaction forming fibrous projections 3.

At this moment, fibrous projections 3 can have a different surface area by changing the size of the silicon particles, the oxygen atmosphere, or the high temperature atmosphere, for example. Thus, fibrous projections 3 can be coated on base 44 to have different surface areas depending on a region.

As described above, fibrous projections 3 made of silicon particles eliminates the need to attach catalyst particles to base 44 in advance. Thus, fibrous projections 3 can be applied onto base 44 made of various materials without being limited by the heat resistance of base 44. In this case, base 44 is not directly joined to fibrous projections 3. However, fibrous projections 3 may be directly joined to base 44 by increasing the temperature to a predetermined value after fibrous projections 3 are applied. When base 44 made of, e.g. glass, fibrous projections 3 can be directly joined to base 44 by increasing the temperature to about 500° C.

By forming fibrous projection 3 on base 44 made of an ITO substrate including a light-transmissive electrode, the interaction in the reaction field can be tested by an electrical measurement with an electric field applied thereto.

Fibrous projections 3 can be formed only on a surface layer of silicon particles. In this case, the silicon particle layer has thereon a layer consisting of fibrous projections 3. Thus, even a very-thin layer of fibrous projections 3 can be formed without being broken.

Figure 8:
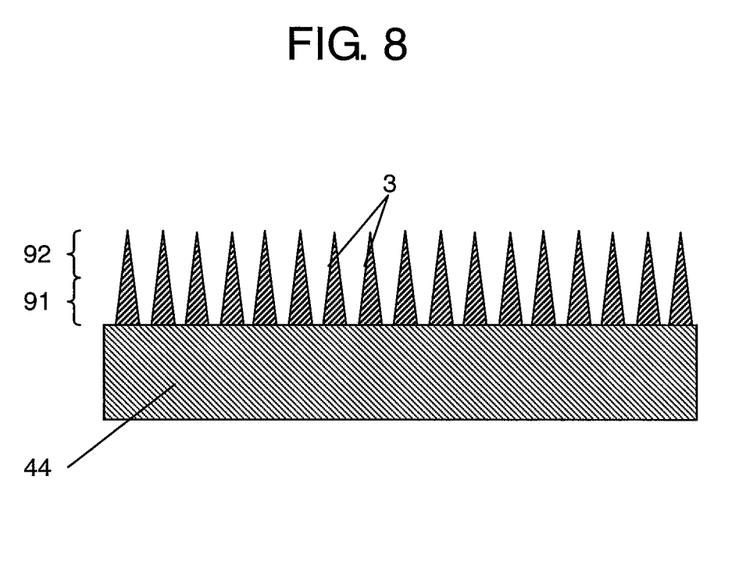
FIG. 8 is a cross-sectional view of another sensor substrate according to Embodiment 1.

As shown in FIG. 8, Fibrous projections 3 can be formed in a conical shape. Since the shape of fibrous projection 3 is a conical shape, the surface area changes continually from fixed end-side region 91 to free end-side region 92. Therefore, a clean spot can be formed.

Exemplary Embodiment 2

Figure 7:
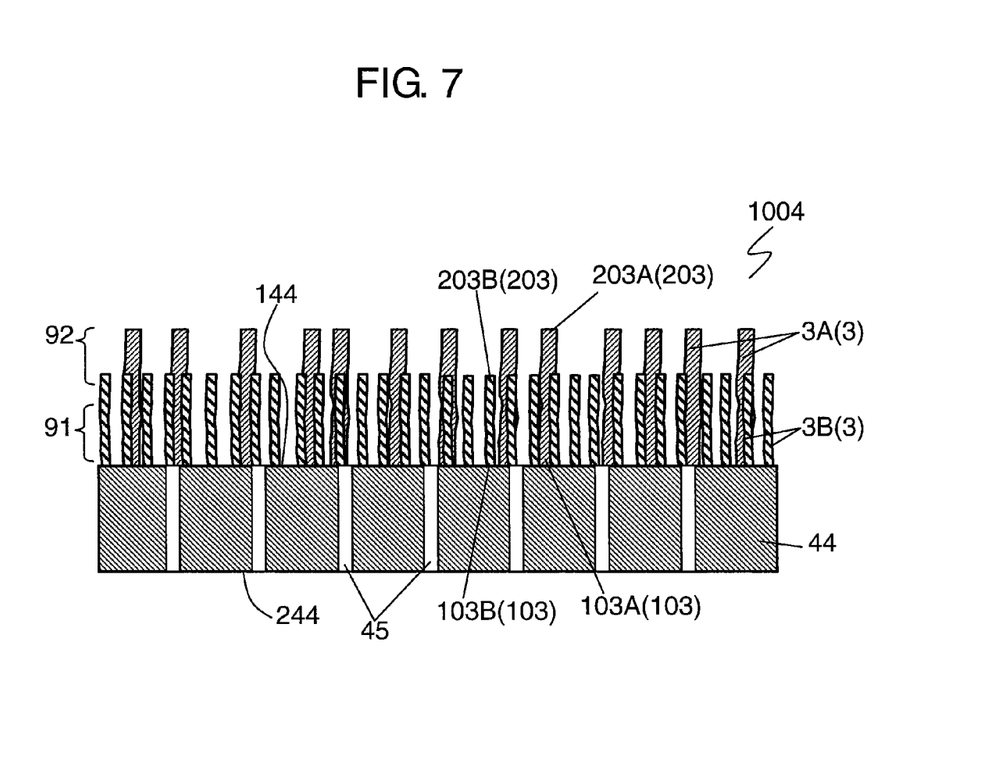
FIG. 7 is a cross-sectional view of a sensor substrate according to Exemplary Embodiment 2 of the disclosure.

FIG. 7 is a cross-sectional view of sensor substrate 1004 according to Exemplary Embodiment 2. In this embodiment, sensor substrate 1004 functions as a filter.

In FIG. 7, components identical to those of sensor substrate 1002 according to Embodiment 1 shown in FIG. 2 are denoted by the same reference numerals.

Sensor substrate 1004 includes base 44 and fibrous projections 3 directly joined to upper surface 144 of base 44. Fibrous projections 3 mainly contain silicon oxide. Base 44 has through-holes 45 that pass through base 44 from upper surface 144 to lower surface 244 opposite to upper surface 144.

When a sensor substrate is used as a filter, the sensor substrate has been generally made of porous material. The sensor substrate made of porous material has substantially the same porous condition at any part. Thus, liquid may permeate to an unnecessary range or permeates insufficiently.

In order for the filter liquid to effectively pass through the through-holes, it is required that liquid is dripped onto the fibrous substance without expanding to an unnecessary range and the liquid can permeate only the fibrous substance of a predetermined region. Specifically, if solution is filtered by a filter made of a fibrous substance that has an excessively-high water retention rate, the liquid cannot be filtered efficiently. If solution is filtered by a filter made of a water-repellent fibrous substance that has a low water retention rate, the solution may be scattered.

In sensor substrate 1004 according to Embodiment 2, liquid dripped to free end-side region 92 passes through through-holes 45 to reach lower surface 244 of base 44. In sensor substrate 1004, fibrous projections 3(3A) formed in free end-side region 92 have a high water retention rate, and thus, can suppress the scattering of the solution during the permeation of the liquid. Furthermore, fibrous projections 3(3A, 3B) positioned in fixed end-side region 91 have a low water retention rate, thus suppressing the permeated liquid from expanding to an unnecessary range. This structure through which liquid can be filtered efficiently provides sensor substrate 1004 with a high filtering efficiency.

The present disclosure is not limited to Embodiments 1 and 2. In Embodiments 1 and 2, terms, such as "upper surface" and "lower surface", indicating directions indicate relative directions depending only on positional relationship of components, such as base 44 and fibrous projection 3, of the sensor substrate, and do not indicate absolute directions, such as a vertical direction.

INDUSTRIAL APPLICABILITY

A sensor substrate according to the present disclosure has a high detection accuracy and is useful as an array substrate, such as a DNA array substrate, a protein array substrate, or a filter.

REFERENCE MARKS IN THE DRAWINGS 3, 3A, 3B Fibrous Projection
44 Base
45 Through-Holes
91 Fixed End-Side Region
92 Free End-Side Region
103 Fixed End
203 Free End
1001 Array Substrate
1002, 1003, 1004 Sensor Substrate

The invention claimed is:

1. A sensor substrate comprising:
a base having an upper surface; and
a plurality of fibrous projections provided on the upper surface of the base, wherein:
the plurality of fibrous projections have a plurality of fixed ends fixed to the upper surface of the base and a plurality of free ends opposite to the fixed ends, respectively,
the plurality of fibrous projections form a fixed end-side region including the plurality of fixed ends of the plurality of fibrous projections and a free end-side region including the plurality of free ends of the plurality of fibrous projections,
the plurality of fibrous projections include first fibrous projections and second fibrous projections,
an average diameter of the first fibrous projections is greater than an average diameter of the second fibrous projections, wherein an average length of the first fibrous projections is greater than an average length of the second fibrous projections, and
a total surface area of the plurality of fibrous projections in the fixed end-side region is larger than that in the free end-side region.

2. The sensor substrate according to claim 1, wherein an interval of fibrous projections in the fixed end-side region is smaller than that in the free end-side region.

3. The sensor substrate according to claim 1, wherein the plurality of fibrous projections are arranged in a mesh arrangement in the fixed end-side region.

4. The sensor substrate according to claim 1, wherein a liquid diffusion rate in the fixed end-side region is lower than that in the free end-side region.

5. The sensor substrate according to claim 4, wherein the free end region has a width equal to or shorter than a half of a length from the plurality of free ends to the plurality of fixed ends.

6. The sensor substrate according to claim 1, wherein the plurality of fibrous projections are made of silicon oxide.

7. The sensor substrate according to claim 1, wherein the plurality of fibrous projections are made of amorphous silicon dioxide.

8. The sensor substrate according to claim 1, wherein the plurality of fibrous projections are directly joined to the upper surface of the base.

9. The sensor substrate according to claim 1, wherein the base has a plurality of through-holes passing through the base from the upper surface to a lower surface of the base.

10. The sensor substrate according to claim 6, wherein:
the base is made of a silicon containing material, and
a silicon atom at the upper surface of the base is covalently-linked to a silicon atom in the plurality of fibrous projection.

11. The sensor substrate according to claim 1, wherein the upper surface of the base includes a layer made of silicone dioxide.

12. An array substrate comprising:
a plurality of sensor substrates arranged in an array shape, wherein at least one of the plurality of sensor substrates is the sensor substrate according to of claim 1.

13. A sensor substrate comprising:
a base having an upper surface; and
a plurality of fibrous projections provided on the upper surface of the base, wherein:
the plurality of fibrous projections have a plurality of fixed ends fixed to the upper surface of the base and a plurality of free ends opposite to the plurality of fixed ends, respectively,
the plurality of fibrous projections provide a fixed end-side region including the plurality of fixed ends of the plurality of fibrous projections and a free end-side region including the plurality of free ends of the plurality of fibrous projections,
the plurality of fibrous projections include first fibrous projections and second fibrous projections,
an average diameter of the first fibrous projections is greater than an average diameter of the second fibrous projections, wherein an average length of the first fibrous projections is greater than an average length of the second fibrous projections, and
a porosity of a portion around the plurality of fibrous projections in the free end-side region is higher than that in the fixed end-side region.

14. The sensor substrate according to claim 13, wherein the base has a plurality of through-holes passing through the base from the upper surface to a lower surface of the base.

15. The sensor substrate according to claim 13, wherein:
the base and the plurality of fibrous projections includes silicon, and
a silicon atom at the upper surface of the base is covalently-linked to a silicon atom in the plurality of fibrous projections.

16. The sensor substrate according to claim 13, wherein the upper surface of the base includes a layer made of silicone dioxide.

17. An array substrate comprising:
a plurality of sensor substrates arranged in an array shape, wherein at least one of the plurality of sensor substrates is the sensor substrate according to claim 13.

18. The sensor substrate according to claim 1, wherein the fixed end-side region includes the first and second fibrous projections and the free end-side region includes no second fibrous projections.

* * * * *